US009493778B2

(12) United States Patent
Tracy et al.

(10) Patent No.: US 9,493,778 B2
(45) Date of Patent: Nov. 15, 2016

(54) METHODS AND COMPOSITIONS FOR GENETICALLY MANIPULATING CLOSTRIDIA AND RELATED BACTERIA WITH HOMOLOGOUS RECOMBINATION ASSOCIATED PROTEINS

(71) Applicant: Elcriton, Inc., New Castle, DE (US)

(72) Inventors: Bryan Tracy, Wilmington, DE (US); Eleftherios Papoutsakis, Newark, DE (US)

(73) Assignee: Elcriton, Inc., Newark, DE (US)

( * ) Notice: Subject to any disclaimer, the term of this patent is extended or adjusted under 35 U.S.C. 154(b) by 87 days.

(21) Appl. No.: 13/826,953

(22) Filed: Mar. 14, 2013

(65) Prior Publication Data

US 2013/0203170 A1 Aug. 8, 2013

Related U.S. Application Data

(63) Continuation-in-part of application No. 12/948,887, filed on Nov. 18, 2010, now abandoned.

(60) Provisional application No. 61/262,288, filed on Nov. 18, 2009.

(51) Int. Cl.
*C12N 15/74* (2006.01)
*C07K 14/33* (2006.01)
*C12N 15/10* (2006.01)

(52) U.S. Cl.
CPC .............. *C12N 15/74* (2013.01); *C07K 14/33* (2013.01); *C12N 15/1082* (2013.01)

(58) Field of Classification Search
None
See application file for complete search history.

(56) References Cited

U.S. PATENT DOCUMENTS

| | | |
|---|---|---|
| 2006/0228799 A1 | 10/2006 | Pati et al. |
| 2008/0085558 A1 | 4/2008 | Soucaille et al. |
| 2010/0047890 A1 | 2/2010 | Tracy et al. |
| 2010/0075424 A1 | 3/2010 | Tracy et al. |
| 2010/0159553 A1 | 6/2010 | Bradin |

OTHER PUBLICATIONS

Canas et al. The RecU Holliday junction resolvase acts at early stages of homologous recombination. Nucleic Acids Res. Sep. 2008;36(16):5242-9.*
Fernandez, Silvia, et al., "Genetic Recombination in Bacillus subtilis 168: Effects of RecU and RecS Mutations on DNA Repair and Homologous Recombination", Journal of Bacteriology, vol. 180, No. 13, Jul. 1998, pp. 3405-3409.
Fraser, Christophe, et al., "Recombination and the Nature of Bacterial Speciation", Science, vol. 315, Jan. 26, 2007, pp. 476-480.
Green, Edward M., et al., "Genetic Manipulation of Acid Formation Pathways by Gene Inactivation in Clostridium acetobutylicum ATCC 824", Microbiology (1996), vol. 142, pp. 2079-2086.
Green, Edward M., et al., "Inactivation of an Aldehyde/Alcohol Dehydrogenase Gene from Clostridium acetobutylicum ATCC 824", Applied Biochemistry and Biotechnology, vol. 57/58, 1996, pp. 213-221.
Gupta, Phalguni, et al., "Chromosomal Engineering of Clostridium perfringens Using Group II Introns", Methods in Molecular Biology, vol. 435: Chromosomal Mutagenesis, pp. 217-228, (2008).
Shao, Lijun, et al., "Targeted Gene Disruption by Use of a Group II Intron (Targetron) Vector in Clostridium acetobutylicum", Cell Research (2007), 17, pp. 963-965.
Sillers, Ryan, et al., "Metabolic Engineering of the Non-Sporulating, Non-Solventogenic Clostridium acetobutylicum Strain M5 to Produce Butanol Without Acetone Demonstrate the Robustness of the Acid-Formation Pathways and the Importance of the Electron Balance", Metabolic Engineering, 10, (2008), pp. 321-332.
Straathof, Adrie J.J., et al., "Feasibility of Acrylic Acid Production by Fermentation", Appl. Microbiol Biotechnology, 2005, 67, pp. 727-734.
Tolonen, Andrew C., et al., "Targeted Gene Inactivation in Clostridium phytofermentans Shows that Cellulose Degradation Requires the Family 9 Hydrolase Cphy3367", Molecular Microbiology (2009), 74(6), pp. 1300-1313.
Raju, Deepa, et al., "Investigating the Role of Small, Acid-Soluble Spore Proteins (SASPs) in the Resistance of Clostridium perfringens Spores to Heat", BMC Microbiology 2006, vol. 6, pp. 50-62.
Rocha, Eduardo P. C., et al., "Comparative and Evolutionary Analysis of the Bacterial Homologous Recombination Systems", PLoS Genetics, Aug. 2005, vol. 1, Issue 2, pp. 0247-0259.
Sabathe Fabrice, et al., "Characterization of the CipA Scaffolding Protein and In Vivo Production of a Minicellulosome in Clostridium acetobutylicum", Journal of Bacteriology, vol. 185, No. 3, Feb. 2003, pp. 1092-1096.
Soucaille, Phillippe, et al., "Gene deletion and integration without markers in Clostridium acetobutylicum", Session III: Genetics and Genomic of Non-Pathogenic Clostridia, Conference on Non-Pathogenic Bacteria, Feb. 24-27, 2008, 4 Pages.
Sarker, Mahfuzur R., et al., "Inactivation of the gene (cpe) encoding Clostridium perfringens enterotoxin eliminates the Ability of two cpe-positive V. perfringens type A human gastrointestinal disease isolates to affect rabbit ileal loops", Molecular Microbiology (1999), 33(5), pp. 946-958.
Papoutsakis, Eleftherios Terry, et al., "Fermentaion Equations for Propionic-Acid Bacteria and Production of Assorted Oxychemicals from Various Sugars", Biotechnology and Bioengineering, vol. 27, Jan. 1985, pp. 67-80.
Papoutsakis, Eleftherios T., "Engineering Solventogenic Clostridia", Current Opinion in Biotechnology, 2008, 19, pp. 420-429.
Perret, Stephanie, et al., "Towards Designer Cellulosomes in Clostridia: Mannanase Enrichment of the Cellulosomes Produced by Clostridium cellulolyticum", Journal of Bacteriology, Oct. 2004, vol. 186, No. 19, pp. 6544-6552.

(Continued)

*Primary Examiner* — Jim Ketter
(74) *Attorney, Agent, or Firm* — McCarter & English, LLP (57) ABSTRACT

Methods for enhancing single cross-over homologous recombination in gram positive bacteria are presented. These methods provide enhanced capability to genetically modify gram positive bacteria.

14 Claims, 3 Drawing Sheets

(56) References Cited

OTHER PUBLICATIONS

Perret, S., et al., "Production of Heterologous and Chimeric Scaffoldins by Clostridium acetobutylicum ATCC 824", Journal of Bacteriology, Jan. 2004, vol. 186, No. 1, pp. 253-257.
Paredes, Carlos J., "A Comparative Genomic View of Clostridial Sporulation and Physiology", Nature Reviews—Microbiology, vol. 3, No. 12, Dec. 2005, pp. 969-978.
Lilley, David J., et al. "The Junction-Resolving Enzymes"; Nature Reviews—Molecular Cell Biology, vol. 2, Jun. 2001, pp. 433-443.
Harris, Latonia M., et al., "Northern, Morphological, and Fermentation Analysis of spo0A Inactivation and Overexpression in Clostridium acetobutylicum ATCC 824", Journal of Bacteriology, Jul. 2002, vol. 184, No. 13, pp. 3586-3597.
Heap, John T., et al., "The ClosTron: A Universal Gene Knock-out System for the Genus Clostridium", Journal of Microbiological Methods, 70, (2007), pp. 452-464.
Hillmann, Falk, et al., "PerR Acts as a Switch for Oxygen Tolerance in the Strict Anaerobe Clostridium acetobutylicum", Molecular Microbiology, (2008), 68(4), pp. 848-860.
Hiom, Kevin, "Homologous Recombination", Current Biology, vol. 10, No. 10, pp. R359-R361, (2000).
Huang, I-Hsiu, et al., "Disruption of the Gene (spo0A) Encoding Sporulation Transcription Factor Blocks Endospore Formation and Enterotoxin Production in Enterotoxigenic Clostridium perfringens Type A", FEMS Microbiology Letters 233 (2004), pp. 233-240.
Hughes, Joseph B., et al., "Anaerobic Biotransformation of 2,4-Dinitrotoluene and 2,6 Dinitrotoluene by Clostridium acetobutylicum; A Pathway Through Dihydroxylamino Intermediates", Environmental Science & Technology, vol. 33, No. 7, 1999, pp. 1065-1070.
Jones, Shawn W., et al., "The Transcriptional Program Underlying the Physiology of Clostridial Sporulation", Genome Biology, 2008, vol. 9, Issue 7, Article R114, pp. 1-21.
Karberg, Michael, et al., "Group II Introns as Controllable Gene Targeting Vectors for Genetic Manipulation of Bacteria", Nature Biotechnology, vol. 19, Dec. 2001, pp. 1162-1167.
Keis, Stefanie, et al., "Taxonomy and Phylogeny of Industrial Solvent-Producing Clostridia", International Journal of Systematic Bacteriology, vol. 45, No. 4, Oct. 1995, pp. 693-705.
Kelly, Stephen J., et al. "Structure, Flexibility, and Mechanism of the Bacillus stearothermophilus RecU Holliday Junction Resolvase", Proteins, 2007, vol. 68, pp. 961-971.
Kowalczykowski, Stephen C. "Initiation of Genetic Recombination and Recombination-Dependent Replication", TIBS 25, Apr. 2000, pp. 156-165.
Borden, Jacob R., et al., "Dynamics of Genomic-Library Enrichment and Identification of Solvent Tolerance Genes for Clostridium acetobutylicum", Applied and Environmental Microbiology, vol. 73, No. 9, May 2007, pp. 3061-3068.
Carrasco, Begona, et al., "Genetic Recombination in Bacillus subtilis 168: Contribution of Holliday Junction Processing Functions in Chromosome Segregation", Journal of Bacteriology, vol. 186, No. 17, Sep. 2004, pp. 5557-5566.
Carrasco, Begona, et al., "Bacillus subtilis RecU Holliday-Junction Resolvase Modulates RecA Activities", Nucleic Acids Research, 2005, vol. 33, No. 12, pp. 3942-3952.
Desai, Ruchir P., et al.,"Antisense RNA Strategies for Metabolic Engineering of Clostridium acetobutylicum", Applied and Environmental Microbiology, vol. 65, No. 3, Mar. 1999, pp. 936-945.
Doi, Roy H., et al., "Cellulosomes: Plant-Cell-Wall-Degrading Enzyme Complexes", Nature Reviews—Microbiology, vol. 2, Jul. 2004, pp. 541-551.
Nolling, Jork, et al., "Genome Sequence and Comparative Analysis of the Solvent-Producing Bacterium Clostridium acetobutylicum", Journal of Bacteriology, Aug. 2001, vol. 183, No. 16, pp. 4823-4838.
O'Brien, David K., et al., "Effects of Clostridium perfringens Alpha-Toxin (PLC) and Perfringolysin O (PFO) on Cytotoxicity to Macrophages, on Escape from the Phagosomes of Macrophages, and on Persistence of C. perfringens in Host Tissues", Infection and Immunity, Sep. 2004, vol. 72, No. 9, pp. 5204-5215.
McGregor, Natalie, et al., "The Structure of Bacillus subtilis RecU Holliday Junction Resolvase and Its Role in Substrate Selection and Sequence-Specific Cleavage", Structure, vol. 13, Sep. 2005, pp. 1341-1351.
Mermelstein, Lee D., et al., "In Vivo Methylation in Escherichia coli by the Bacillus subtilis Phage o3T I Methyltransferase to Protect Plasmids from Restriction upon Transformation of Clostridium acetobutylicum ATCC 824", Applied and Environmental Microbiology, Apr. 1993, vol. 59, No. 4, pp. 1077-1081.
Mermelstein, Lee D., "Expression of Cloned Homologous Fermentative Genes in Clostridium acetobutylicum ATCC 824", Biotechnology, vol. 10, Feb. 1992, pp. 190-195.
Mingardon, Florence, et al., Heterologous Production, Assembly, and Secretion of a Minicellulosome by Clostridium acetobutylicum ATCC 824, Applied and Environmental Microbiology, Mar. 2005, vol. 71, No. 3, pp. 1215-1222.
Montoya, D., et al., "New solvent-producing *Clostridium* sp. strains, hydrolyzing a wide range of polysaccharides, are closely related to *Clostridium butyricum*", Journal of Industrial Mocrobiology & Biotechnology, (2001), 27, pp. 329-335.
Lorenz, Michael G., et al., "Bacterial Gene Transfer by Natural Genetic Transformation in the Environment", Microbiological Reviews, Sep. 1994, vol. 58, No. 3, pp. 563-602.
Liu, Hong, et al., "Production of Electricity from Acetate or Butyrate Using a Single-Chamber Microbial Fuel Cell", Environmental Science & Technology, vol. 39, No. 2, 2005, pp. 658-662.
Lee, Song F., et al., "Cellulolytic Activity of Clostridium acetobutylicum", Applied and Environmental Microbiology, vol. 50, No. 2, Aug. 1985, pp. 220-228.
Longtine, Mark S., et al., "Additional Modules for Versatile and Economical PCR-based Gene Deletion and Modification in *Saccharomyces cerevisiae*", Yeast, 14, (1998), pp. 953-961.
Lee, Song F., et al., "Xylanolytic Activity of Clostridium acetobutylicum", Applied and Environmental Microbiology, vol. 50, No. 4, Oct. 1985, pp. 1068-1076.
Duckett, Derek R., et al., "The Structure of the Holliday Junction, and Its Resolution", Cell, vol. 55, Oct. 7, 1988, pp. 79-89.
Young, Michael, et al. "Genetic Exchange and Prospects for Cloning in Clostridia", Bacillus Molecular Genetics and Biotechnology Applications, 1986, Academic Press, Inc., pp. 259-281.
Duwat et al. A general method for cloning recA genes of gram-positive bacteria by polymerase chain reaction. J Bacteriol. Aug. 1992;174(15):5171-5.
Fernandez et al. Bacillus subtilis homologous recombination: genes and products. Res Microbiol. Jul.-Aug. 2000;151(6):481-6.
Mermelstein et al. Metabolic engineering of Clostridium acetobutylicum ATCC 824 for increased solvent production by W enhancement of acetone formation enzyme activities using a synthetic acetone operon. 5;42(9):1053-60, (1993).

* cited by examiner

METHODS AND COMPOSITIONS FOR GENETICALLY MANIPULATING CLOSTRIDIA AND RELATED BACTERIA WITH HOMOLOGOUS RECOMBINATION ASSOCIATED PROTEINS

CROSS REFERENCE TO RELATED APPLICATIONS

This application is a continuation-in-part application of U.S. application Ser. No. 12/948,887, filed Nov. 18, 2012, and claims priority from U.S. Provisional Patent Application No. 61/262,288, filed Nov. 18, 2009, both of which are incorporated herein by reference in entirety.

FIELD OF THE INVENTION

The present invention relates to methods and compositions for genetically manipulating bacterial cells, particularly a cell of the class Clostridia, but also related bacteria which are difficult to genetically manipulate due to lack of an effective recombination system. In particular, embodiments of the present invention relate to the expression of recombinant homologous recombination proteins in Clostridia and in other bacterial species.

BACKGROUND OF THE INVENTION

Clostridia and Its Potential Use in Industry

Rising and unstable prices for petroleum based chemicals and fuels have resulted in renewed interest in their production via alternative approaches (e.g. biochemical approaches). Coupled with concerns of global climate change and securing a domestic source of transportation fuels, efforts are being focused towards the fermentative conversion of inexpensive renewable feedstocks (biomass) to fuel alcohols and chemicals. Such processes have been employed for over a century at very large scale, but advanced genetic and metabolic engineering approaches for generating second-generation chemical and fuel producing microbes are required for making these current ventures commercially viable.

Clostridia are strictly anaerobic, endospore forming prokaryotes of major importance to cellulose degradation, human and animal health and physiology, anaerobic degradation of simple and complex carbohydrates, acidogenesis, and bioremediation of complex organics [10]. Solventogenic, butyric-acid clostridia (e.g., *Clostridium acetobutylicum, C. beijerinckii* and *C. butyricum*) [11] played a major industrial role in the production of acetone and butanol in the past (and likely now and in the future) by the Acetone-Butanol-Ethanol fermentation (ABE) (Jones and Woods 1986; Rogers 1986; Lesnik, Sampath et al. 2001). Significantly, metabolic engineering of solventogenic clostridia, as recently reviewed [9], may lead to industrial processes for production of additional chemicals such as butyric acid, butanediol, propanol, and acetoin (Jones and Woods 1986; Rogers 1986; Lesnik, Sampath et al. 2001), production of hydrogen [12] or for biotransformations [13]. Some of these chemicals (butanol, ethanol) can serve as biofuels directly, while others can be used for chemical conversion to biofuels (e.g., butyric acid [14]) or the generation of electricity [12]. Related clostridia can produce additional chemicals such as propionic and acrylic acids [15] [16]. Finally, clostridia, as might be expected from these ancient anaerobic soil organisms, have a great potential for applications in bioremediation [17].

Based on the fundamental and applied importance of this genus, the DOE has completed the genome sequence [18] of *C. acetobutylicum* ATCC 824 ("Cac"). A number of metabolic engineering tools have been developed for this genus of bacteria such as recombinant DNA expression plasmids [19], antisense RNA approaches [20], and gene expression libraries [21]. However, the full potential of any industrially relevant species will not be fully realized until an efficient chromosomal integration system is developed that allows for more elaborate and stable genetic manipulations of the host. Such a system would ideally be suitable for all Clostridia species, capable of disrupting selected genes, capable of integrating large pieces of recombinant DNA into the host chromosome, and easily and rapidly implemented in any research and R&D setting (academic or industrial). Methods for gene inactivation in clostridia have been inefficient, first based on non-replicating vectors [22], and later using a replicating vector (Harris, Welker et al. 2002). Unfortunately, these methods have not been generally successful for inactivating genes.

Most recently, the TargeTron™ system (group II intron principle) was adapted to clostridia by two different groups (Heap, Pennington et al. 2007; Shao, Hu et al. 2007). There are also two other more recently reported methods, the first method was developed by the research group of Dr. P. Soucaille at INSA of Toulouse, in collaboration with the company Metabolic Explorer. They developed a novel endonuclease expression technique to digest replicating plasmid DNA into linear disruption cassettes within the clostridia host that can then recombine via homologous recombination into the target chromosomal region, [23], [24]. A suicide plasmid approach was developed and used to knockout acid-formation genes in the Cac asporogenous mutant M5 [25]. However, both of these approaches are severely limited.

First, the group II intron and endonuclease based methods have not demonstrated the ability to incorporate more than about 1.5 kB of DNA into the chromosome, and the majority of the 1.5 kB is consumed by a selection marker. Second, the suicide approach has only been demonstrated in one specific strain of *C. acetobutylicum,* the M5 strain, and has yet to succeed in any other clostridia strain.

Homologous Recombination

Homologous recombination is a housekeeping process involved in the maintenance of chromosome integrity and generation of genetic variability that is nearly ubiquitous to all microorganisms [26-28]. The cellular machinery involved is not necessarily conserved, but the general series of events is common to all microorganisms studied to date. The typical series of events for homologous recombination are initiation, strand-invasion, strand-exchange, and Holliday junction resolution [28-30]. Within specific classes of bacteria, the proteins involved in homologous recombination are fairly well conserved.

Absense, Importance and Utility of Resolvase Expression

The most essential protein in the later stages of homologous recombination is the resolvase. Resolvases are a well-known class of proteins that perform a key role in Holliday-junction resolution. There are a number of distinct resolvase enzymes, and resolvase activity is ubiquitous to nearly all bacteria [28, 31]. Holliday-junctions are four-way DNA intermediate complexes formed during homologous recombination [32]. There are two major resolvases found on the genomes of Gram-negative and Gram-positive bacteria. These are ruvC and recU, respectively [28, 33]. The significance of resolvases, and more specifically of recU in Gram-positive organisms was studied via deletion mutants and tested by the deficiency in DNA repair and intramolecular recombination [33-35]. These studies strongly support the essential role of RecU in Holliday-junction resolution for Gram-positive organisms, such as clostridia and bacilli. Subsequent studies determined high-resolution structures of RecU from *Bacillus subtilis* and *B. stearothermophilus* and proposed detailed models for how the RecU protein physically interacts with the Holliday-junction [36, 37]. A recent comparative genomic analysis suggests that clostridia do not contain genes for any recognizable resolvase protein [28]. Thus, we hypothesized that the lack of resolvase activity is responsible for the experimental difficulty in generating homologous recombination events for gene disruptions in all clostridia [38].

The analysis by Rocha et al. [28] demonstrated the absence of resolvase activity in *Clostridium perfringens, C. tetani* and Cac, the only clostridia genomes analyzed. Significantly only 10 genomes out of the 110 analyzed appeared to be resolvase deficient. Of those 10, four were void of any sort of recombination system.

SUMMARY OF THE INVENTION

A method is described for enhancing single-crossover homologous recombination in a population of bacteria. The method comprises combinatorially expressing recombinant RecO, Rec A, or RecG with RecU, wherein recombinant bacteria are produced.

DETAILED DESCRIPTION OF THE INVENTION

To further extend the analysis of Rocha [28], we performed our own homology searches of the *B. subtilis* recU gene against six annotated or draft clostridia genome sequences, based upon the first round of orthology assignment performed in the Rocha et al. paper. The final analysis included Cac, *C. perfringens, C. tetani, C. difficile* 630, *C. novyi* NT, *C. thermocellum, C. beijerincki,* and *C. cellulolyticum.* All genomes were void of any discernible RecU resolvase, which is the conserved resolvase for Gram-positive organisms.

We then tested the hypothesis that RecU expression in clostridia will result in efficient recombination. Specifically, we over-expressed the heterologous resolvase from *B. subtilis,* RecU (coded by recU), in Cac under the control of the strong Cac thiolase promoter. For this, we used a replicating plasmid that contained two contiguous regions of homology for a gene on the Cac chromosome. Initial investigations targeted the sigma factor sigE, which is a known transcriptional regulator in clostridia sporulation and possibly also solvent formation [10]. The final plasmid, targeted against a specific gene is referred to as a site-specific chromosomal integration plasmid (SSCI plasmid). For sigE we refer to this as the sigE SSCI plasmid. The two regions of homology were disrupted by a thiamphenicol (TH) antibiotic resistance gene. There was also an erythromycin (EM) antibiotic resistance gene on the plasmid, outside of the regions of homology. Therefore if a double crossover event between the host chromosome and plasmid were to occur, the TH marker would be incorporated into the chromosome and the EM marker would be lost upon plasmid curing, which describes the loss of the plasmid. If a single crossover occurred, both TH and EM markers would be incorporated in the chromosome, but EM resistance would not be as strong upon plasmid curing, because cells require multiple copies of the EM resistance gene to be very EM resistant. A single copy of the TH resistance gene is sufficient for strong TH resistance.

Our results, described in US 2010/0075424, showed that although resolvase expression improved single-crossover efficiency, double-crossover homologous recombination was rarely observed. Therefore, we hypothesized that homologous recombination proteins are not well-expressed and/or are down-regulated during exponential growth, the period of culture during which we believe homologous recombination is occurring.

In view of these results, we have developed a novel approach for genetically altering clostridia via recombinant expression of the homologous recombination associated proteins RecO, RecG, and RecA derived from any heterologous source that is naturally compatible (i.e. can be transcribed and translated) or engineered to be compatible (e.g. codon usage of heterologous gene is varied to be readily transcribed in the bacteria host) in any clostridia species or other difficult to genetically manipulate species. Expression can be independent or combinatorial, i.e., in combination, particularly with RecU. We have demonstrated that during independent or combinatorial expression, homologous recombination is stimulated at higher frequency than in the absence of recombinant homologous recombination protein expression. Additionally, we demonstrate that this approach is feasible and will be genetically feasible in many other clostridial species, particularly *C. botulinum, C. difficile, C. perfringens, C. tetanii, C. sporogenes, C. novyi, C. acetobutylicum, C. pasteurianum, C. beijerinckii, C. ljungdahlii, C. carboxidivorans, C. thermocellum, C. cellulolyticum, C. phytofermentans, C. tyrobutyricum, C. butyricum, C. kluyveri, C. sticklandii, Moorella thermoacetica, C. autoethanogenum, C. ragsdalei, Moorella thermoautotrophica, C. propionicum, C. thermobufyricum, C. thermoaceticum, C. formicoaceticum,* and *Butyribacterium methylotrophicum.*

This method involves recombinant expression of any individual or combination of the homologous recombination proteins RecG, RecO or RecA in any clostridial host or related bacterial species. The source of the recG, recO or recA can be any natural or engineered heterologous gene. Specific applications include complementing a clostridial or related species with the aforementioned genes. The genes can be expressed individually, in combination, from a site-specific chromosome targeted integration plasmid, from a separate plasmid, or from chromosomal integration into a host organism. The expression is used for gene knockins, gene knockouts, constructing gene knockin/knockout libraries, creating chromosomal expressed fusion proteins, etc.

The following examples describe methods for enhancing the capability to genetically modify clostridial species, including 1) enhanced frequency for site-specific homologous recombination by independent recombinant expression of a homologous recombination protein, 2) enhanced frequency of site-specific homologous recombination by combinatorial recombinant expression of homologous recombination proteins (particularly with RecU), and 3) enhanced frequency of site-specific double crossover homologous recombination by combinatorial recombinant expression of homologous recombination proteins (particularly with RecU).

EXAMPLES

Example 1

Analysis of Publicly Available DNA Microarray Data for Expression of Homologous Recombination Proteins in *Clostridium acetobutylicum*

Figure 1:
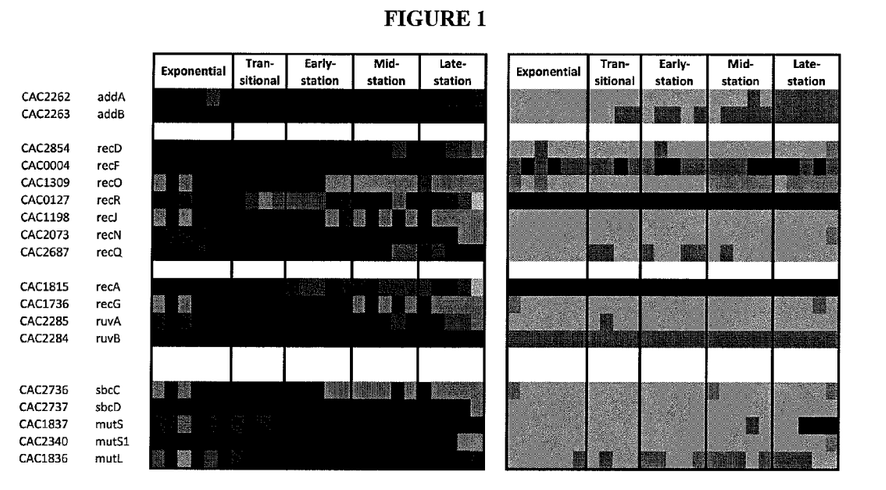
FIG. 1 is a DNA-microarray analysis of the essential homologous recombination proteins for Cac. Expression data is shown as both differential expression (left) and expression intensity (right). For differential expression, green indicates down-regulated compared to the pooled RNA from the entire time course and red indicates up-regulated. For the expression intensity, darker blue indicates the gene exhibited higher fluorescence intensity for specific probes on the microarray against all other genes and lighter blue indicates the gene exhibited lower fluorescence intensity for specific probes on the microarray against all other genes. Grey indicates time points at which a gene was not differentially expressed or did not generate a detectable signal on the microarray.

We analyzed the expression profiles and absolute expression levels of each homologous recombination proteins from a detailed time profile of a batch culture of the WT Cac strain (ATCC824) [50]. Expression profiles refer to the differential expression of the gene in each growth phase (exponential, transition, early-stationary, mid-stationary and late-stationary), which was determined by hybridizing cDNA from a specific period of growth against a pool of cDNA from all periods of growth. The expression level was determined by ranking each gene from the full genome microarray on a percentage scale of 0 to 100. Genes with greater expression at a specific time point, as determined by greater fluorescence intensity on the microarray, are ranked closer to 100. Genes that showed very low intensity were ranked closer to 0. The results are shown in FIG. 1.

Based upon the microarray analysis, differential expression suggests that a number of homologous recombination initiation proteins are up-regulated during exponential growth, such as recO, recN, recJ and recD. However, the most important "strand exchange" protein, RecA, is down-regulated during exponential growth. Looking at the expression rankings, it suggests that recO and recG are very lowly expressed (<23rd percentile ranking for all time points for recO and <31st percentile for recG). Based upon these findings and recU over-expression results, we believe homologous recombination can be enhanced by over-expressing recO, recG and/or recA.

Example 2

Assess the Feasibility of Stimulating Recombination via Expression of Homologous Recombination Proteins in Conjunction With RecU Based upon our findings from the DNA-microarray transcriptional analysis, as discussed above, we believe that RecG, RecO and RecA are ideal targets for over-expression. Additionally we will test the expression of a heterologous RecA (from *B. subtilis*) since this approach was successful with the *B. subtilis* resolvase (RecU) expression.

2.A: To Express Homologous Recombination Proteins From a Replicating, Site-Specific Chromosomal Integration Plasmid (SSCI Plasmid)

Each homologous recombination protein (RecO, RecG, endogenous RecA and heterologous RecA) will be PCR amplified from Cac genomic DNA with an appended thiolase promoter ($P_{thl}$) on the 5'-primer and a rho-independent transcription terminator sequence on the 3'-primer. The thiolase promoter is a strong, growth-associated promoter, commonly used in Cac for gene over-expression, and was used in our previous studies with RecU expression. The rho-independent terminator is a palindromic sequence that forms a stem-loop, hairpin structure when transcribed, causing the RNA polymerase to dissociate from the DNA thus terminating transcription. Due to the presence of the $P_{thl}$ and the rho-independent terminator, each PCR product is a single transcriptional unit. The resulting PCR products will be individually cloned into the sigE-targeted, replicating, SSCI plasmid (sigE-SSCI plasmid). This is the same SSCI plasmid we previously employed for disrupting the sigE locus via a single crossover event with RecU over-expression, thus already has RecU over-expression.

Figure 2:
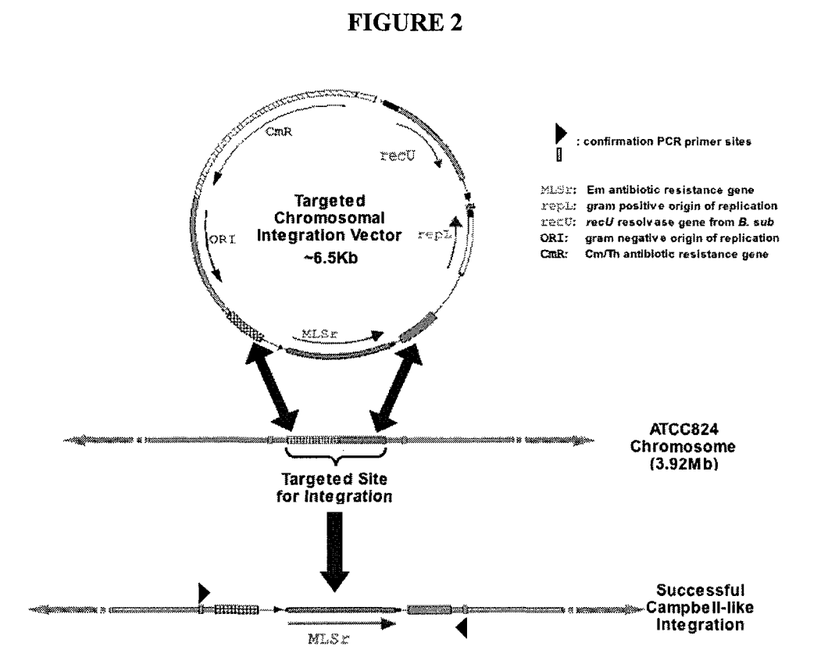
FIG. 2 is a schematic of a SSCI plasmid incorporating into its targeted genomic region through a double crossover integration, which is commonly believed to occur via a Campbell-like mechanism. This schematic differs from what is described in Task 1 by the antibiotic markers being switched. The schematic shows the EM marker (MLSr) being present in the disruption cassette and the TH marker being on the plasmid backbone. However, to screen for single crossovers, the EM marker must be on the vector backbone and TH marker in the disruption cassette.

The 5' region of homology is 253 basepairs (bp) and the 3' region is 306 bp. The regions of homology are contiguous to the targeted region of the chromosome, and are disrupted on the plasmid by a thiamphenicol (TH) antibiotic resistance marker (refer to FIG. 2 for a schematic of such a plasmid and integration event). The regions of homology and disrupting TH marker (also a chloramphenicol (CM) resistance marker in *E. coli*) are collectively referred to as the disruption cassette. In addition to the disruption cassette, the SSCI plasmid contains an erythromycin (EM) antibiotic marker and origins of replication for both Gram-negative and Gram-positive bacteria, which we collectively refer to as the plasmid backbone. The plasmid is shuttled through a strain of *E. coli* containing methylase activity, which methylates the SSCI plasmid prior to transforming Cac [51]. Cac is electrotransformed via a well-established protocol developed in the Papoutsakis' lab (Mermelstein, Welker et al. 1992; Mermelstein and Papoutsakis 1993) and transformants are confirmed via TH and EM resistance. Expression of each homologous recombination protein will be confirmed by reverse transcription PCR.

2.B: Inducing and Screening for Site-Specific Chromosomal Integration (SSCI)

To induce SSCI, we grow cells harboring the SSCI plasmid for 5 days under vegetative growth conditions and under TH selection. This is done by replica plating cells every 24 hours onto a fresh nutrient plate with TH selection. Cells grow exponentially to create a "lawn" of growth within 24 hours and are then replica plated again with velveteen squares and a replica-plating device. TH selection is maintained for a period of 5 days in order to either maintain cells harboring the SSCI plasmid or to maintain cells that have integrated the SSCI plasmid into the chromosome via either a single or double crossover event. A single-crossover event incorporates the entire SSCI plasmid (disruption cassette and plasmid backbone), and a double-crossover event replaces the endogenous regions of homology with the disruption cassette, and excises the SSCI plasmid backbone. Therefore, SSCI plasmid harboring cells, single-crossover and double-crossover cells will be maintained during the TH replica plating. Cells that lose the plasmid and have not undergone a crossover event will be lost from the population.

Prior to screening, we "cure" cells of the SSCI plasmid by replica plating for 5 days under vegetative growth conditions without any antibiotic selection. During this time, cells are likely to lose the replicating plasmid since there is no selection for its maintenance, but copies of the TH marker that have integrated into the chromosome are maintained. Additionally, copies of the EM marker that have integrated into the chromosome via single-crossover events are also maintained, unless a second crossover event occurs and excises out the plasmid backbone.

For screening, plates are replica plated after the 5th day of no antibiotic pressure onto fresh nutrient plates with TH selection. Cells that were "cured" of the plasmid and did not undergo a crossover event will be lost from the population under TH selection. Cells are allowed to grow for 24 hours under TH selection and then replica plated onto fresh nutrient plates with EM selection. Cells that still harbor the SSCI plasmid or have undergone a single-crossover event will grow on the EM plates in 24 to 48 hours. Cells that have plasmid borne resistance to EM grow within 24 hours of replica plating. Cells that have single-crossover, chromosomal borne EM resistance require at least 36 and more often 48 hours to grow because there is only a single copy of the EM resistance gene compared to 5 -15 copies from the replicating SSCI plasmid (the average copy number of these plasmids is 7). Cells that do not grow at all on EM plates, but do grow on TH are indicative of double-crossover events. Table 1 outlines the selection criteria and likely explanation for each cell type.

TABLE 1

| TH Resistance | EM resistance | Likely Genotype |
|---|---|---|
| + | − | Double-cross |
| + | + | Single-cross |
| + | ++ | Plasmid |
| − | − | No cross or plasmid |

The possible phenotypes from SSCI screening and the likely genotype associated with each phenotype.
"Cross" = crossover.

2.C: Confirming Site-Specific Chromosomal Integration and Determining the Relative Effectiveness of Each Homologous Recombination Protein Expression in Conjunction With RecU The current standard for confirming SSCI is sequencing the genomic region about which the integration event occurred. For double-crossover integrations, this is a simple task of PCR amplifying the region where integration occurred (refer to FIG. 3). We will use PCR primers (Conf-F and Conf-R) flanking the regions of homology where the integration is expected to occur. PCR product should include the chromosomal region and the disrupting TH marker. This is then sequenced for confirmation.

Figure 3:
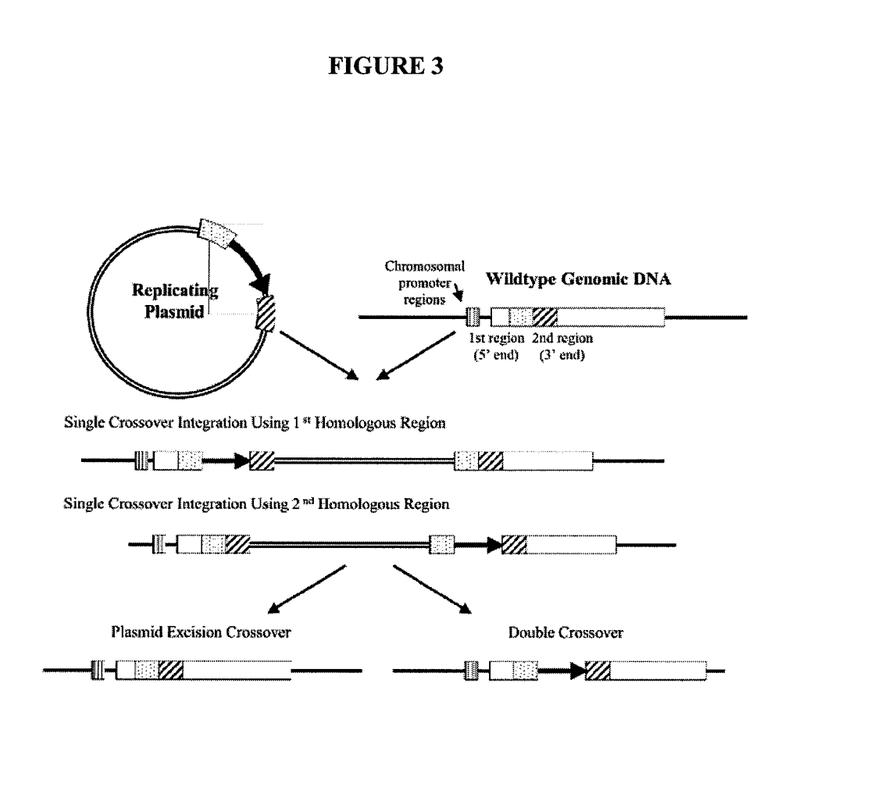
FIG. 3 is a schematic of all possible integration events and the PCR reactions performed to determine the nature of the integration. PCR primers are as listed: red—Conf-F; blue—Conf-R; green—CM/TH-F; and yellow—CM/TH-R.

In the case of single-crossover integrations, the PCR amplification of the region of integration is not easy to perform because the PCR product would typically be greater than 6000 by and will be susceptible to a lot of mispriming due to incomplete product extension. However, by knowing the orientation of the TH marker in relation to the gene we are attempting to disrupt (i.e., whether the TH marker is in the same or opposite coding strand of the gene of interest), we can perform two PCR reactions to determine if crossover occurred through the first or second region of homology. This is depicted in FIG. 3. If in the same coding strand, a single-crossover through the first region of homology is confirmed by a ~1500 by PCR product, when using the PCR primer combination of Conf-F and CM/TH-R. The Conf-F refers to the 5' flanking PCR primer for the region of integration and the CM/TH-R refers to the 3' PCR primer for amplifying the TH marker. If crossover occurred through the second region of homology you will obtain a ~1500 by PCR product when using the PCR primer combination of Conf-R and CM/TH-F. The Conf-R refers to the 3' flanking PCR primer for the region of integration and the CM/TH-F refers to the 5' PCR primer for amplifying the TH marker. If the TH marker and disrupted gene sequence are in opposite coding strands you would employ different primer sets and expect different results from the PCR reactions. Table 2 outlines the appropriate primer sets for confirming which region of homology a single-crossover occurred for both orientations of TH marker and disrupted gene.

TABLE 2

| Orientation of CM/TH marker in relation to disrupted gene sequence | Appropriate primer sets for confirming region of integration | Results from colony PCR(+, PCR product; −, no PCR product) | Interpretation of PCR results |
|---|---|---|---|
| CM/TH and disrupted gene sequence are in the same coding strand | 1. Conf-F with CM/TH-R<br>2. Conf-R with CM/TH-F | 1. +<br>2. − | Integration through $1^{st}$ region of homology |
| | 1. Con-F with CM/TH-R<br>2. Conf-R with CM/TH-F | 1. −<br>2. + | Integration through $2^{nd}$ region of homology |
| CM/TH and disrupted gene sequence are in opposite coding strands | 1. Conf-R with CM/TH-R<br>2. Conf-F with CM/TH-F | 1. +<br>2. − | Integration through $1^{st}$ region of homology |
| | 1. Conf-R with CM/TH-R<br>2. Conf-F with CM/TH-F | 1. −<br>2. + | Integration through $2^{nd}$ region of homology |

Table 2. List of appropriate primer sets to use when confirming a single integration event through the 1$^{st}$ and 2$^{nd}$ region of homology. The table also details possible results and the most probable explanation of such results.

Eventually we need to determine the exact sequence of the entire region of integration. So after confirming a putative single-crossover clone by the aforementioned PCR method, we will perform XL (extra-long) PCR reactions under an assortment of reaction and annealing temperature conditions to obtain specific and large quantities of PCR product that can then be sequenced.

To determine the relative overall effectiveness of each homologous recombination protein in conjunction with RecU at stimulating and enhancing recombination, we first determine whether single or double-crossovers occur at all. Our comparison control is the sigE-SSCI plasmid without any homologous recombination protein expression. Previously, such experiments never generated single of double-crossover events without the expression of the RecU protein. Thus the ability to generate either a single or double-crossover event is a positive outcome. However, there are no established protocols for quantitatively determining the effectiveness of stimulating homologous recombination. Therefore we propose the following semi-quantitative approach, which will likely be necessary for comparing the results from each homologous protein expression against each other.

Semi-quantitative analysis will be performed by first quantifying the physical area on each TH screening plate that indicates single or double crossover integration. Subsequently we will determine the frequency of single and double-crossover events per colony screened as determined by PCR confirmation. This value, multiplied by the physical area of single or double integration from the TH screening plates will represent the relative effectiveness (RE) for enhancing and stimulating chromosomal integration.

Example 3

Feasibility Analysis of Further Enhancing Homologous Recombination via the Resolvase Only Over-Expression by Varying Length of Homologous DNA and the Presentation of the Disruption Cassette 3.A: The Impact of the Length of the Homologous Regions for Recombination As mentioned, the majority of our experiments have and will continue to use regions of homology that are 250-300 by long. However, most of the clostridia literature that has attempted chromosomal integration via homologous recombination reports using regions of homology that are significantly longer. Therefore we will test 1000, 500, 250 and 100 bp regions of homology for obtaining integration into the sigE locus. We will construct new disruption cassettes and clone them into the already made sigE-SSCI plasmid that contains the RecU-P$_{thl}$ expression vector. We will stimulate, screen, confirm and determine the relative effectiveness of enhancing recombination for each length of homology by the methods described above. See Example 5.

3.B: Varying the Presentation of DNA for Homologous Recombination: Linear DNA Versus Circular DNA on a Suicide Plasmid Versus Circular DNA on a Replicating Plasmid Other common approaches for integrating DNA into the chromosome include linear DNA (i.e. the Longtine approach employed in yeast [52]) and suicide/non-replicating plasmids, which has been reported in Cac but cannot be routinely performed. We will attempt these same approaches by creating the strain 824(pRecU), which expresses RecU-P$_{thl}$ from a separate plasmid than the SSCI plasmid.

EM resistance provided on the pRecU plasmid will maintain RecU expression. We will transform 824(pRecU) with either a linear DNA-disruption cassette or a suicide SSCI plasmid that contains a disruption cassette but no origin of replication for Gram-positive organisms, such as pAKKO from a recent publication from the Papoutsakis group [25]. Transformants that survive TH selection theoretically must have undergone a chromosomal integration event because suicide plasmids and linear DNA cannot replicate. In this approach, RecU is under the expression of the strong, growth-associated thiolase promoter. Thus, at the time of transformation, the competent cells should be actively expressing RecU and RecU will serve the same purpose of promoting recombination as demonstrated via the replicating SSCI plasmid approach. RecU expression will again be verified by reverse transcription PCR. Resulting TH resistant mutants are readily cured of the pRecU plasmid by vegetatively transferring without EM selection. We will test a range of DNA amounts for each approach, from 50 μg to 0.1 μg of DNA per transformation. We typically use 0.5 μg of DNA for transforming a replicating plasmid. We will stimulate, screen, confirm and determine the relative success at enhancing recombination by the methods described previously.

Example 4

Overexpression of RecO and RecU Improves the Frequency of Homologous Recombination in Clostridia An "over-expression cassette" was used for recombinant over-expression of RecO or RecA in combination with over-expression of RecU. The over-expression cassette contained RecU under the control of the phosphotransbutyrylase promoter (P$_{ptb}$) on a replicating plasmid, (pKORSIGE, described in US 2010/0075424), that is targeted for site-specific disruption of the sigE gene, (CAC1695, described in US 2010/0047890 and US 2010/0075424, both of which are incorporated in entirety herein by reference). RecO and RecA were each cloned into separate sigE-SSCI plasmids under the control of the P$_{ptb}$ promoter, as described in Example 2. The P$_{ptb}$ promoter acts as a strong, constitutive-like promoter in Clostridia and yields overexpression, e.g., at least twice wild type expression, of each recombinant protein. RecA from *Bacillus subtilus* (RecA(Bsu)) was expressed from the natural promoter instead of P$_{ptb}$.

Site-specific chromosomal integration was induced and detected as described in Examples 2B and 2C. Results are shown in Table 3. Minimal integration frequency (MIF) was calculated as number of CFUs exhibiting slow EM growth divided by number of CFUs exhibiting fast EM growth. No double-crossover integration was observed for any of the strains. RecO strains exhibited notably higher single-crossover integration frequencies than RecU only strains. RecA strains performed slightly better than RecU only strains, but less robustly than RecO strains. Single-crossover integration frequencies in RecA(Bsu) strains was much lower than in RecU only strains. These results demonstrate that concomitant overexpression of homologous RecO and heterologous RecU enhances the frequency of homologous recombination in *C. acetobutylicum*.

TABLE 3

| Strain | Minimal integration freq. (MIF) | Standard deviation | MIF improvement |
|---|---|---|---|
| $P_{ptb}$-recO | 63% | 5.9% | 91% |
| $P_{ptb}$-recA | 38% | 5.9% | 15% |
| recA(Bsu) | 8% | 11.7% | −76% |
| $P_{ptb}$-recU | 33% | 11.7% | NA |

Example 5

Length of Homology can be Optimized to Enhance the Efficiency of Homologous Recombination in Clostridia The sigE-SSCI plasmids used in Example 4 each contained two regions of homology to sigE of approximately 250 bp. The effect of varying the length of the regions of homology on minimal integration frequency was examined using the siE-SSCI plasmid for RecU only, having two regions of homology of 100, 250, 500 or 1000 bp. Results are shown in Table 4.

Substantially higher single-crossover integration was observed with 1000 bp regions of homology. Homology over 500 by yielded only slightly higher frequencies than 250 bp. Homology over 100 bp yielded the same frequency of integration as 250 bp of homology.

TABLE 4

| Strain | Minimal integration freq. (MIF) | Standard deviation | MIF improvement |
|---|---|---|---|
| 100 bp | 33% | 1.0% | 0% |
| 500 bp | 38% | 5.9% | 15% |
| 1000 bp | 71% | 5.9% | 115% |
| $P_{ptb}$-recU | 33% | 11.7% | NA |

REFERENCES

1. Doi, R. H. and A. Kosugi, Cellulosomes: Plant-cell-wall-degrading enzyme complexes. Nature Reviews Microbiology, 2004. 2(7): p. 541-51.
2. Lee, S. F., C. W. Forsberg, and L. N. Gibbins, Xylanolytic Activity of Clostridium-Acetobutylicum. Applied and Environmental Microbiology, 1985. 50(4): p. 1068-76.
3. Lee, S. F., C. W. Forsberg, and L. N. Gibbins, Cellulolytic Activity of Clostridium-Acetobutylicum. Applied and Environmental Microbiology, 1985. 50(2): p. 220-8.
4. Montoya, D., C. Arevalo, S. Gonzales, F. Aristizabal, and W. H. Schwarz, New solvent-producing Clostridium sp strains, hydrolyzing a wide range of polysaccharides, are closely related to Clostridium butyricum. Journal of Industrial Microbiology & Biotechnology, 2001. 27(5): p. 329-35.
5. Mingardon, F., S. Perret, A. Belaich, C. Tardif, J. P. Belaich, and H. P. Fierobe, Heterologous production, assembly, and secretion of a minicellulosome by Clostridium acetobutylicum ATCC 824. Applied and Environmental Microbiology, 2005. 71(3): p. 1215-22.
6. Perret, S., A. Belaich, H. P. Fierobe, J. P. Belaich, and C. Tardif, Towards designer cellulosomes in clostridia: Mannanase enrichment of the cellulosomes produced by Clostridium cellulolyticum. Journal of Bacteriology, 2004. 186(19): p. 6544-52.
7. Perret, S., L. Casalot, H. P. Fierobe, C. Tardif, F. Sabathe, J. P. Belaich, and A. Belaich, Production of heterologous and chimeric scaffoldins by Clostridium acetobutylicum ATCC 824. Journal of Bacteriology, 2004. 186(1): p. 253-7.
8. Sabathe, F. and P. Soucaille, Characterization of the CipA scaffolding protein and in vivo production of a mini-cellulosome in Clostridium acetobutylicum. Journal of Bacteriology, 2003. 185(3): p. 1092-6.
9. Papoutsakis, E. T., Engineering solventogenic clostridia. Current Opinion in Biotechnology, 2008. 19(5): p. 420-9.
10. Paredes, C. J., K. Alsaker, and E. T. Papoutsakis, A comparative genomic view of clostridial sporulation and physiology. Nature Reviews Microbiology, 2005. 3(12): p. 969-78.
11. Keis, S., C. F. Bennett, V. K. Ward, and D. T. Jones, Taxonomy and phylogeny of industrial solvent-producing clostridia. International Journal of Systematic Bacteriology, 1995. 45(4): p. 693-705.
12. Liu, H., S. A. Cheng, and B. E. Logan, Production of electricity from acetate or butyrate using a single-chamber microbial fuel cell. Environmental Science & Technology, 2005. 39(2): p. 658-62.
13. Young, M., M. E. Collins, J. D. Oultram, and A. Pennock, Genetic exchange and prospects for cloning in Clostridia, in Bacillus molecular genetics and biotechnology applications, A. T. Ganeson and J. A. Hoch, Editors. 1986, Academic Press: Orlando. p. 259-81.
14. Bradin, D., Preparing hexane, useful in gasoline composition, comprises fermenting a sugar using yeast or bacteria to give butyric acid and subjecting the butyric acid to Kolbe electrolysis/photo-Kolbe electrolysis and isolating the hexane. 2007, CPS BIOFUELS INC (CPSB-Non-standard).
15. Straathof, A. J., S. Sie, T. T. Franco, and L. A. van der Wielen, Feasibility of acrylic acid production by fermentation. Appl Microbiol Biotechnol, 2005. 67(6): p. 727-34.
16. Papoutsakis, E. T. and C. L. Meyer, Fermentation Equations for Propionic-Acid Bacteria and Production of Assorted Oxychemicals from Various Sugars. Biotechnology and Bioengineering, 1985. 27(1): p. 67-80.
17. Hughes, J. B., C. Y. Wang, and C. L. Zhang, Anaerobic biotransformation of 2,4-dinitrotoluene and 2,6-dinitrotoluene by Clostridium acetobutylicum: A pathway through dihydroxylamino intermediates. Environmental Science & Technology, 1999. 33(7): p. 1065-70.
18. Nölling, J., G. Breton, M. V. Omelchenko, K. S. Makarova, Q. Zeng, R. Gibson, H. M. Lee, J. Dubois, D. Qiu, J. Hitti, Y. Wolf, R. L. Tatusov, F. Sabathe, L. Doucette-Stamm, P. Soucaille, M. J. Daly, G. N. Bennett, E. V. Koonin, and D. R. Smith, Genome sequence and comparative analysis of the solvent-producing bacterium Clostridium acetobutylicum. Journal of Bacteriology, 2001. 183(6): p. 4823-38.
19. Mermelstein, L. D., N. E. Welker, G. N. Bennett, and E. T. Papoutsakis, Expression of cloned homologous fermentative genes in Clostridium acetobutylicum ATCC 824. Biotechnology (N Y), 1992. 10(2): p. 190-5.
20. Desai, R. P. and E. T. Papoutsakis, Antisense RNA strategies for the metabolic engineering of Clostridium acetobutylicum. Applied and Environmental Microbiology, 1999. 65(3): p. 936-45.
21. Borden, J. R. and E. T. Papoutsakis, Dynamics of genomic-library enrichment and identification of solvent-tolerance genes in Clostridium acetobutylicum Appl Environ Microbiol, 2007. 73: p. 3061-8.

22. Green, E. M., Z. L. Boynton, L. M. Harris, F. B. Rudolph, E. T. Papoutsakis, and G. N. Bennett, Genetic manipulation of acid formation pathways by gene inactivation in Clostridium acetobutylicum ATCC 824. Microbiology, 1996. 142(Pt 8): p. 2079-86.

23. Soucaille, P., R. Figge, and C. Croux, Replacing a target DNA sequence by homologous recombination in Clostridia by transforming the strain with a vector comprising an origin of replication permitting its replication in Clostridia, and a replacement cassette, METABOLIC EXPLORER (META-Non-standard) SOUCAILLE P (SOUC-Individual) FIGGE R (FIGG-Individual) CROUX C (CROU-Individual). p. 1908840-A8:.

24. Hillmann, F., R. J. Fischer, F. Saint-Prix, L. Girbal, and H. Bahl, PerR acts as a switch for oxygen tolerance in the strict anaerobe Clostridium acetobutylicum. Mol Microbiol, 2008. 68(4): p. 848-60.

25. Sillers, R., A. Chow, B. Tracy, and E. T. Papoutsakis, Metabolic engineering of the non-sporulating, non-solventogenic Clostridium acetobutylicum strain M5 to produce butanol without acetone demonstrate the robustness of the acid-formation pathways and the importance of the electron balance. Metabolic Engineering, 2008. doi:10.1016/j.ymben.2008.07.005

26. Fraser, C., W. P. Hanage, and B. G. Spratt, Recombination and the nature of bacterial speciation. Science, 2007. 315(5811): p. 476-80.

27. Lorenz, M. G. and W. Wackernagel, Bacterial gene transfer by natural genetic transformation in the environment. Microbiol Rev, 1994. 58(3): p. 563-602.

28. Rocha, E. P., E. Cornet, and B. Michel, Comparative and evolutionary analysis of the bacterial homologous recombination systems. PLoS Genet, 2005. 1(2): p. e15.

29. Hiom, K., Homologous recombination. Curr Biol, 2000. 10(10): p. R359-61.

30. Kowalczykowski, S. C., Initiation of genetic recombination and recombination-dependent replication. Trends Biochem Sci, 2000. 25(4): p. 156-65.

31. Lilley, D. M. and M. F. White, The junction-resolving enzymes. Nat Rev Mol Cell Biol, 2001. 2(6): p. 433-43.

32. Duckett, D. R., A. I. Murchie, S. Diekmann, E. von Kitzing, B. Kemper, and D. M. Lilley, The structure of the Holliday junction, and its resolution. Cell, 1988. 55(1): p. 79-89.

33. Fernandez, S., A. Sorokin, and J. C. Alonso, Genetic recombination in Bacillus subtilis 168: effects of recU and recS mutations on DNA repair and homologous recombination. J Bacteriol, 1998. 180(13): p. 3405-9.

34. Carrasco, B., S. Ayora, R. Lurz, and J. C. Alonso, Bacillus subtilis RecU Holliday-junction resolvase modulates RecA activities. Nucleic Acids Res, 2005. 33(12): p. 3942-52.

35. Carrasco, B., M. C. Cozar, R. Lurz, J. C. Alonso, and S. Ayora, Genetic recombination in Bacillus subtilis 168: contribution of Holliday junction processing functions in chromosome segregation. J Bacteriol, 2004. 186(17): p. 5557-66.

36. Kelly, S. J., J. Li, P. Setlow, and M. J. Jedrzejas, Structure, flexibility, and mechanism of the Bacillus stearothermophilus RecU Holliday junction resolvase. Proteins, 2007. 68(4): p. 961-71.

37. McGregor, N., S. Ayora, S. Sedelnikova, B. Carrasco, J. C. Alonso, P. Thaw, and J. Rafferty, The structure of Bacillus subtilis RecU Holliday junction resolvase and its role in substrate selection and sequence-specific cleavage. Structure, 2005. 13(9): p. 1341-51.

38. Heap, J. T., O. J. Pennington, S. T. Cartman, G. P. Carter, and N. P. Minton, The ClosTron: A universal gene knock-out system for the genus Clostridium. J Microbiol Methods, 2007. 70(3): p. 452-64.

39. Green, E. M. and G. N. Bennett, Inactivation of an aldehyde/alcohol dehydrogenase gene from Clostridium acetobutylicum ATCC 824. Appl Biochem Biotechnol, 1996. 57-58: p. 213-21.

40. Harris, L. M., N. E. Welker, and E. T. Papoutsakis, Northern, morphological, and fermentation analysis of spo0A inactivation and overexpression in Clostridium acetobutylicum ATCC 824. Journal of Bacteriology, 2002. 184(13): p. 3586-97.

41. Saint-Prix, F., M. Gonzalez-Pajuelo, C. Croux, L. Girbal, and P. Soucaille. Development of a system for chromosomal integration and gene deletion in Clostridium acetobutylicum ATCC824. in Clostridium IX. 2006. Houston, Tex., USA.

42. Huang, I. H., M. Waters, R. R. Grau, and M. R. Sarker, Disruption of the gene (spo0A) encoding sporulation transcription factor blocks endospore formation and enterotoxin production in enterotoxigenic Clostridium perfringens type A. FEMS Microbiol. Lett., 2004. 233(2): p. 233-40.

43. Raju, D., M. Waters, P. Setlow, and M. R. Sarker, Investigating the role of small, acid-soluble spore proteins (SASPs) in the resistance of Clostridium perfringens spores to heat. BMC Microbiol, 2006. 6: p. 50.

44. Sarker, M. R., R. J. Carman, and B. A. McClane, Inactivation of the gene (cpe) encoding Clostridium perfringens enterotoxin eliminates the ability of two cpe-positive C. perfringens type A human gastrointestinal disease isolates to affect rabbit ileal loops. Mol Microbiol, 1999. 33(5): p. 946-58.

45. O'Brien, D. K. and S. B. Melville, Effects of Clostridium perfringens alpha-toxin (PLC) and perfringolysin O (PFO) on cytotoxicity to macrophages, on escape from the phagosomes of macrophages, and on persistence of *C. perfringens* in host tissues. Infect Immun, 2004. 72(9): p. 5204-15.

46. Gupta, P. and Y. Chen, Chromosomal engineering of *Clostridium perfringens* using group II introns. Methods Mol Biol, 2008. 435: p. 217-28.

47. Shao, L., S. Hu, Y. Yang, Y. Gu, J. Chen, Y. Yang, W. Jiang, and S. Yang, Targeted gene disruption by use of a group II intron (targetron) vector in *Clostridium acetobutylicum*. Cell Res, 2007. 17(11): p. 963-5.

48. Tolonen, A. C., A. C. Chilaka, and G. M. Church, Targeted gene inactivation in *Clostridium phytofermentans* shows that cellulose degradation requires the family 9 hydrolase Cphy3367. Mol Microbiol, 2009.

49. Karberg, M., H. T. Guo, J. Zhong, R. Coon, J. Perutka, and A. M. Lambowitz, Group II introns as controllable gene targeting vectors for genetic manipulation of bacteria. Nature Biotechnology, 2001. 19(12): p. 1162-7.

50. Jones, S. W., C. J. Paredes, B. Tracy, N. Cheng, R. Sillers, R. S. Senger, and E. T. Papoutsakis, The transcriptional program underlying the physiology of clostridial sporulation. Genome Biology, 2008. 9(7): p. 21.

51. Mermelstein, L. D. and E. T. Papoutsakis, In vivo methylation in *Escherichia coli* by the *Bacillus subtilis* phage phi 3T I methyltransferase to protect plasmids from restriction upon transformation of *Clostridium acetobutylicum* ATCC 824. Appl Environ Microbiol, 1993. 59(4): p. 107710-81.

52. Longtine, M. S., A. McKenzie, 3rd, D. J. Demarini, N. G. Shah, A. Wach, A. Brachat, P. Philippsen, and J. R. Pringle, Additional modules for versatile and economical PCR-based gene deletion and modification in *Saccharomyces cerevisiae*. Yeast, 1998. 14(10): p. 953-61.

We claim:

1. A method for enhancing homologous recombination in a population of bacteria of the class Clostridia comprising combinatorially expressing in the bacteria at least one of recombinant RecO with RecU, recombinant RecA with RecU, or recombinant RecG with RecU, thereby producing recombinant Clostridia bacteria, wherein:
    (a) a site-specific single-crossover chromosomal integration occurs at a greater frequency in the recombinant Clostridia bacteria than in Clostridia bacteria lacking recombinant RecU, recombinant RecA, recombinant RecO and recombinant RecG;
    (b) a site-specific double-crossover chromosomal integration occurs at a greater frequency in the recombinant Clostridia bacteria than in Clostridia bacteria lacking recombinant RecU, recombinant RecA, recombinant RecO and recombinant RecG; or
    (c) the homologous recombination frequency is greater in the recombinant Clostridia bacteria than in Clostridia bacteria that does not overexpress recombinant RecU.

2. The method of claim 1, whereby at least one of the recombinant RecO, RecA, RecG or RecU are overexpressed.

3. The method of claim 1, whereby the population of bacteria consists of Gram-positive bacteria.

4. The method of claim 1, whereby the recombinant RecO, RecA, and RecG are expressed from genes from a *Bacillus* species.

5. The method of claim 1, whereby the recombinant RecU is from a *Bacillus* species.

6. A recombinant bacterium of the class Clostridia produced by combinatorially expressing in the bacterium at least one of recombinant RecO with RecU, recombinant RecA with RecU, or recombinant RecG with RecU, wherein:
    (a) a site-specific single-crossover chromosomal integration occurs at a greater frequency in the recombinant Clostridia bacterium than in a Clostridia bacterium lacking recombinant RecU, recombinant RecA, recombinant RecO and recombinant RecG;
    (b) a site-specific double-crossover chromosomal integration occurs at a greater frequency in the recombinant Clostridia bacterium than in a Clostridia bacterium lacking recombinant RecU, recombinant RecA, recombinant RecO and recombinant RecG; or
    (c) the homologous recombination frequency is greater in the recombinant Clostridia bacterium than in a Clostridia bacterium that does not overexpress recombinant RecU.

7. The bacterium of claim 6, wherein the bacterium is a member of the genus *Clostridium*.

8. A recombinant The bacterium of claim 6, wherein the recombinant RecO, RecA and RecG are expressed from genes from a *Bacillus* species.

9. A recombinant Clostridia bacterium comprising recombinant RecU and at least one of recombinant RecA, recombinant RecO or recombinant RecG, wherein:
    (a) a site-specific single-crossover chromosomal integration occurs at a greater frequency in the recombinant Clostridia bacterium than in a Clostridia bacterium lacking recombinant RecU, recombinant RecA, recombinant RecO and recombinant RecG;
    (b) a site-specific double-crossover chromosomal integration occurs at a greater frequency in the recombinant Clostridia bacterium than in a Clostridia bacterium lacking recombinant RecU, recombinant RecA, recombinant RecO and recombinant RecG; or
    (c) the homologous recombination frequency is greater in the recombinant Clostridia bacterium than in a Clostridia bacterium that does not overexpress recombinant RecU.

10. The recombinant Clostridia bacterium of claim 9, wherein at least one of the RecA, RecO, RecG or RecU is expressed from a gene of a *Bacillus* species.

11. The recombinant Clostridia bacterium of claim 9, wherein at least one of the RecA, RecO, RecG or RecU is overexpressed.

12. The recombinant Clostridia bacterium of claim 9, wherein a site-specific single-crossover chromosomal integration occurs at a greater frequency than a Clostridia bacterium lacking recombinant RecU, recombinant RecA, recombinant RecO and recombinant RecG.

13. The recombinant Clostridia bacterium of claim 9, wherein a site-specific double-crossover chromosomal integration occurs at a greater frequency than a Clostridia bacterium lacking recombinant RecU, recombinant RecA, recombinant RecO and recombinant RecG.

14. The recombinant Clostridia bacterium of claim 9, wherein the homologous recombination frequency is greater in a recombinant Clostridia bacterium overexpressing recombinant recU than is the homologous recombination frequency of a Clostridia bacterium that does not overexpress recombinant recU.

* * * * *